United States Patent [19]

Sheppard et al.

[11] Patent Number: 4,643,177
[45] Date of Patent: Feb. 17, 1987

[54] DYNAMIC TRACTION WRIST CAST BRACE

[75] Inventors: Joseph E. Sheppard; Paul C. Dell, both of Micanopy; Peter F. Gearen, Gainesville; Edward S. Bittar, Alachua; Gary J. Miller, Gainesville, all of Fla.

[73] Assignee: University of Florida, Gainesville, Fla.

[21] Appl. No.: 620,024

[22] Filed: Jun. 13, 1984

[51] Int. Cl.[4] .............................................. A61F 5/04
[52] U.S. Cl. ................... 128/84 C; 128/87 R; 128/92 ZK
[58] Field of Search .................. 128/77, 84 R, 84 A, 128/84 B, 84 C, 85, 87 R, 88, 92 R, 87 A, 92 A

[56] References Cited

U.S. PATENT DOCUMENTS

| 2,091,643 | 8/1937 | Longfellow | 128/92 A |
|---|---|---|---|
| 2,438,144 | 3/1948 | Bunyar, Jr. | 128/77 |
| 2,767,708 | 10/1956 | Keropian | 128/77 |
| 3,028,858 | 4/1962 | Cutler | 128/75 |
| 3,878,842 | 4/1975 | Goldberg | 128/84 C |
| 4,265,230 | 5/1981 | Jordan | 128/87 R |
| 4,336,796 | 6/1982 | Andrews et al. | 128/87 R |
| 4,409,970 | 10/1983 | Carrel | 128/92 A |
| 4,440,159 | 4/1984 | Cochran | 128/133 |

FOREIGN PATENT DOCUMENTS 1240313 7/1960 France ........................ 128/92 A Primary Examiner—Gene Mancene
Assistant Examiner—David I. Tarnoff
Attorney, Agent, or Firm—Dennis P. Clarke

[57] ABSTRACT

A brace for treatment of distal radius fractures allows an adjustable range of motion while simultaneously providing for distal traction. The brace has hinges with adjustable stops, the hinges being made of radiolucent material to allow x-rays without the necessity of removing the brace. Adjustable tensioners are used to provide distal traction by way of a metacarpal pin placed in slots in hand members. The brace is adjustable for different size patients.

21 Claims, 5 Drawing Figures

U.S. Patent    Feb. 17, 1987    4,643,177
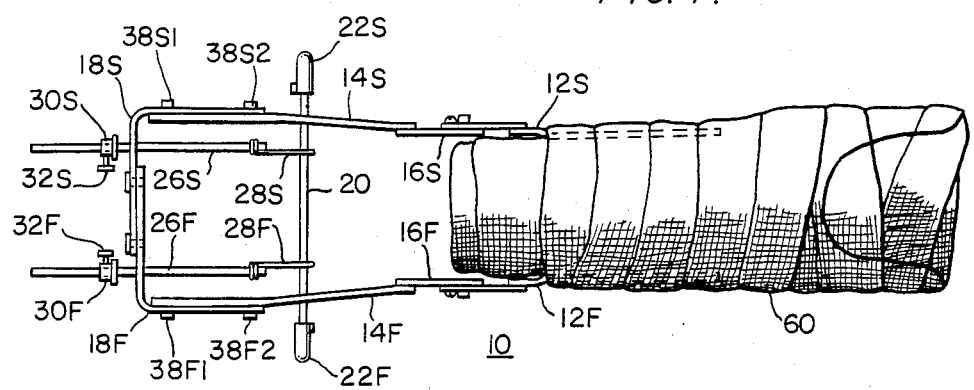
FIG. 1.
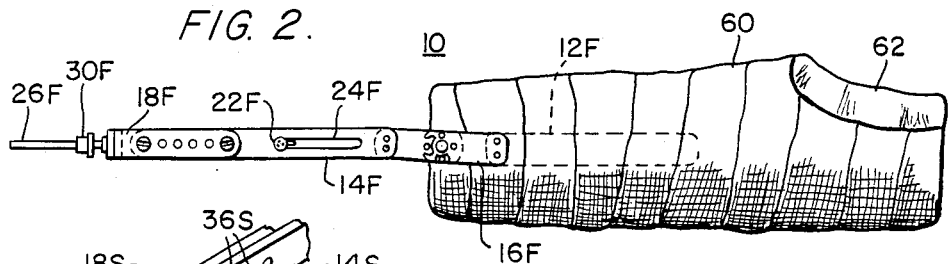
FIG. 2.
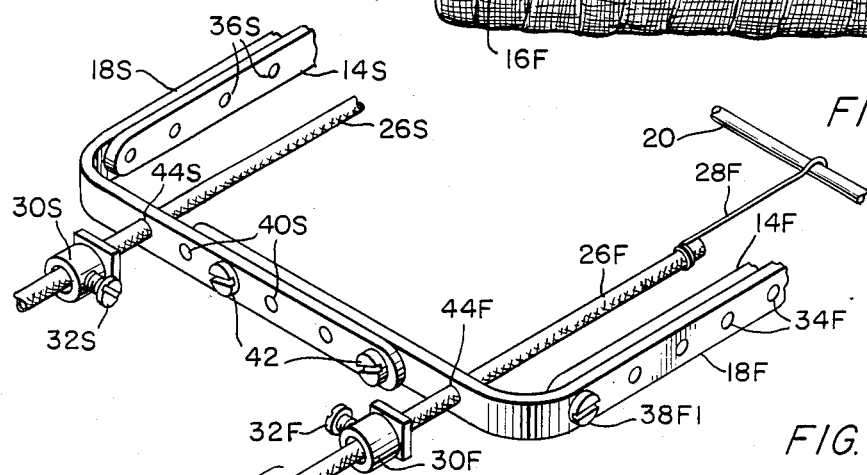
FIG. 3.
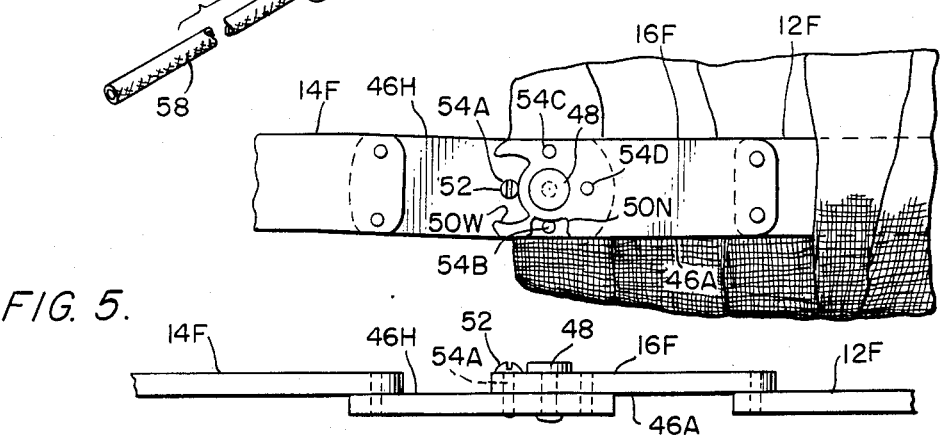
FIG. 4.
FIG. 5.

DYNAMIC TRACTION WRIST CAST BRACE

BACKGROUND OF THE INVENTION

The present invention relates to a wrist cast brace. More specifically, the present invention relates to a wrist cast brace which allows for wrist motion.

Intra-articular fractures, or fractures which extend into the joint, require anatomic reduction and early mobilization whenever this is possible. However, in many circumstances the degree of comminution or bony fragmentation precludes the achievement of a satisfactory reduction. Under these conditions, joint incongruity may lead to progressive degenerative arthritis.

Early motion has been observed experimentally to provide a stimulus for the healing of defects in articular cartilage. Clinically, the use of traction and early motion in comminuted intra-articular fractures has been used to improve joint congruity and to stimulate fibrocartilage repair of the articular cartilage defects.

The following U.S. patents are illustrative of various splints, braces or similar devices: U.S. Pat. Nos. 2,357,323 (Goldberg, Sept. 5, 1944); 2,767,708 (Keropian, Oct. 23, 1956); 3,327,703 (Gamm, June 27, 1967); 3,785,371 (Lewis, Jan. 15, 1974); 3,788,307 (Kistner, Jan. 29, 1974); 4,191,373 (Lancellotti, Mar. 4, 1980); 4,265,230 (Jordon, May 5, 1981); and 4,336,796 (Andrews et al, June 29, 1982).

The Goldberg patent describes a splint with adjustable stops for positioning the metacarpals and maintaining a fixed position. More specifically, a clamp which is slidable within a slot is used to adjust the device depending upon the size of a patient's hand.

The Keropian patent shows an orthopedic brace for the hand of a patient suffering from poliomyelitis. It is adjustable and allows motion through a device which is spring-loaded to aid a patient with muscular problems. The spring allows flexion and extension of the wrist. The device is strapped to the arm. Slots are used to permit sliding of a wrist section of the brace relative to a forearm section of the brace. Metallic hinge pins are used for adjustment purposes.

The Gamm patent discloses an elastic support for stabilization of the wrist and to simultaneously allow flexing movements of the patient's wrist.

The Lewis patent shows an elbow sleeve having adjustable hinge limits to prevent a wearer from flexing his elbow beyond certain points.

The Kistner patent discloses a non-mobile wrist splint with adjustable positioners. It is intended to hold a wearer's wrist in a fixed position.

The Lancellotti patent discloses an elbow brace for treating tennis elbow. The brace includes a slidable connection to allow movement of a forearm section relative to another section.

The Gordon patent shows a traction splint which places tension upon a patient's leg by use of a tether connected to a pin on a splint frame. The joints are held in a fixed position.

The Andrews et al patent shows a distal extremity traction device for the femur. It includes a width adjustment feature having a slot and bolt. However, it does not allow maximum motion at the affected joint.

The use of dynamic traction implementing early knee motion has been accomplished by [Apley, *Apley's System of Orthopaedics and Fractures*, 6th Ed., London, Butterworth Scientific (1982)] for the treatment of tibial plateau fractures.

The concept of distal traction to avoid shortening of forearm length and loss of radiocarpal and radioulnar integrity was developed by [Green, *J. of Bone and Joint Surgery*, 57A:304–310 (1975)] through the use of pins and plaster. However, Green's technique did not allow for wrist motion.

OBJECTS AND SUMMARY OF THE INVENTION

It is a primary object of the present invention to provide a new and improved dynamic traction wrist cast brace.

A more specific object of the present invention is to provide a wrist cast brace allowing a full range of wrist movement simultaneously providing for distal traction.

Another object of the present invention is to provide a wrist cast brace which is readily adjustable for different size patients.

Yet another object of the present invention is to provide a wrist cast brace including adjustable tensioners to adjust the amount of tension applied to the joint.

A still further object of the present invention is to provide a wrist cast brace wherein x-rays may be taken without removal of the brace.

A still further object of the present invention is to provide a wrist cast brace which is adjustable to allow for different ranges of motion of the wrist joint.

The above and other objects of the present invention which will become apparent from the following description are realized by a dynamic traction wrist cast brace comprising: first and second forearm frame members disposed on opposite sides of a forearm cast; first and second hand frame members; first and second hinges respectively pivotably connecting the first and second forearm frame members to the first and second hand frame members, the first and second hinges operable to allow patient wrist motion; a transmetacarpal pin mounted to the first and second hand frame members and slidable relative to the first and second hand frame members, the transmetacarpal pin operable to cause the first and second hand frame members to track movement of a patient's hand; and first and second tensioners respectively attached to first and second sides of the transmetacarpal pin. The brace further comprises first and second end frame members adjustably attached together and adjustably mounted to the respective first and second hand frame members such that the width and length of the brace can be adjusted to fit a particular patient. The first and second end frame members are each adjustably mounted to the respective first and second hand frame members by a series of sequential holes. The transmetacarpal pin is mounted in first and second slots respectively disposed in the first and second hand frame members. The first and second hinges include respective first and second adjustable stop arrangements. The first and second adjustable stop arrangements are each disposable in at least: (i) a first mode allowing the first and second hand frame members to move at least over a 150° range of motion relative to the first and second forearm frame members; (ii) a second mode with a range of motion less than in the first mode; and (iii) a third mode wherein the first and second hand frame members are fixed relative to the first and second forearm frame members. The inclusion of a fourth mode having a range of motion less than the second mode is also a feature of a preferred embodiment of the invention. The first and second adjustable stop arrangements each include a wide radial notch and a narrow radial notch and at least two stop pin receiving holes, and the range of motion of the brace is limited by the wide radial notch when a stop pin is in one of the stop pin receiving holes and the range of motion of the brace is limited by the narrow radial notch when a stop pin is in the other of the stop pin receiving holes. The first and second hinges extend respectively between the first and second forearm frame members and the first and second hand frame members and the first and second hinges are preferably made of radiolucent material such that an x-ray may be made of a patient's wrist without removal of the brace. Each of the first and second tensioners is an elastic band or other tensioning device (e.g., constant tension springs, etc.) adjustably mounted to an end portion extending between the first and second hand frame members.

The present invention may alternately be described as a dynamic traction wrist brace comprising: first and second forearm frame members for disposal on opposite sides of a forearm cast; first and second hand frame members; first and second hinges respectively pivotably connecting the first and second forearm frame members to the first and second hand frame members, the first and second hinges operable to allow patient wrist motion; an end portion extending between the first and second hand frame members; and a transmetacarpal pin mounted to the first and second hand frame members and slidable in slots in the first and second hand frame members, the transmetacarpal pin operable to cause the first and second hand frame members to track movement of a patient's hand. The device further comprises first and second tensioners respectively attached to first and second sides of the transmetacarpal pin and adjustably mounted to the end portion. The end portion comprises first and second end frame members adjustably attached together and adjustably mounted to the respective first and second hand frame members such that the width and length of the brace can be adjusted to fit a particular patient.

The present invention may alternately be described as a dynamic traction wrist brace comprising: first and second forearm frame members for disposal on opposite sides of a forearm cast; first and second hand frame members, the first and second hand frame members respectively attached to the first and second forearm frame members and allowing patient wrist motion; an end portion extending between the first and second hand frame members; a transmetacarpal pin mounted to the first and second hand frame members and slidable in slots in the first and second hand frame members, the transmetacarpal pin operable to cause the first and second hand frame members to track movement of a patient's hand; first and second tensioners respectively attached to first and second sides of the transmetacarpal pin; and first and second end frame members adjustably attached together and adjustably mounted to the respective first and second hand frame members such that the width and length of the brace can be adjusted to fit a particular patient. Each of the first and second tensioners is an elastic band adjustably mounted to one of the first and second end frame members. The device further comprises first and second hinges respectively pivotably connecting the first and second forearm frame members to the first and second hand frame members, the first and second hinges operable to allow wrist motion, and wherein the first and second hinges extend respectively between the first and second forearm frame members and the first and second hand frame members, and the first and second hinges are preferably made of radiolucent material such that an x-ray may be made of a patient's wrist without removal of the brace. The first and second hinges are each disposable in at least: (i) a first mode allowing the first and second hand frame members to move at least over a 150° range of motion relative to the first and second forearm frame members; and (ii) a second mode with a range of motion less than in the first mode.

The present invention also includes a method of using the wrist cast brace or wrist brace described above for the treatment of a fractured bone.

BRIEF DESCRIPTION OF THE DRAWINGS

The above and other features of the present invention will be more easily understood when considered in conjunction with the accompanying drawings wherein like characters represent like parts throughout the several views and in which:

FIG. 1 shows a top view of a dynamic traction wrist cast brace according to the present invention.

FIG. 2 shows a side view of the brace shown in FIG. 1.

FIG. 3 shows a perspective detailed view of an end of the brace of FIG. 1 and FIG. 2.

FIG. 4 shows a detailed side view of an adjustable hinge as used with the present invention.

FIG. 5 shows a top view in detail of the hinge also shown in FIG. 4.

DETAILED DESCRIPTION OF THE DRAWINGS

FIGS. 1 and 2, depict the overall structure of the device of the present invention. The dynamic traction wrist cast brace 10 of the present invention includes first and second forearm frame members 12F and 12S respectively. These forearm frame members 12F and 12S are respectively hingedly connected to first and second hand frame members 14F and 14S by respective hinges 16F and 16S. An end portion comprising first and second end frame members 18F and 18S are respectively mounted to the hand members 14F and 14S. A transmetacarpal pin 20 having plastic end caps 22F and 22S is disposed within slots 24F and a corresponding slot (not shown) in hand frame member 14S.

Elastic tensioners 26F and 26S are respectively attached to first and second sides of the transmetacarpal pin 20 by cord, wire, or other suitable means 28F and 28S. Alternately, the tensioners, 26F and 26S may comprise constant tension springs or any devices capable of imparting constant tension. The tension applied to the transmetacarpal pin 20 by the first and second tensioners 26F and 26S may be adjusted by virtue of first and second adjustable clamps 30F and 30S. As shown, each clamp includes a set screw 32F and 32S which are used to secure the clamps at different positions along the elastic cord 26F and 26S, thereby adjusting the tension on the pin 20.

With further reference to FIGS. 1 and 2, and also considering the detailed perspective view of FIG. 3, the width adjusting and length adjusting features of the present invention are described below. Since the first and second sides of the brace 10 are symmetrical, it will be readily understood that the first hand member 14F and second hand member 14S are identically constructed. Likewise, the first and second end members 18F and 18S are identically constructed. The first hand member 14F is secured to the end member 18F by use of a plurality of holes 34F in the end frame member 18F. These holes (only some of which are labeled) cooperate with similar holes in hand frame member 14F. First and second screws 38F1 and 38F2 are used to secure the end frame member 18F to the hand member 14F. The cooperating holes in hand member 14F are identical to the holes 36S shown for the second hand frame member 14S. Likewise, the screws 38S1 and 38S2 are used for securing the second end frame member 18S to the second hand member 14S.

The end frame member 18S further includes a series of holes 40S into which screws 42 may extend. The screws 42 would further extend through holes in end frame 18F which are identical to the holes 40S in end member 18S.

Depending upon the placement of the screws 38F1, 38F2, 38S1, 38S2, and 42, the brace 10 can be adjusted to accommodate differing lengths and widths depending upon the patient's size.

As shown in FIG. 3, the tension cords 26F and 26S extend through holes 44F and 44S in the respective end members 18F and 18S.

The specific features of the hinge 16F construction are shown in FIGS. 4 and 5. It will be readily appreciated that the hinge 16S is constructed identically to hinge 16F.

The hinge 16F comprises a forearm piece 46A which is riveted to the forearm frame member 12F, and a hand piece 46H which is riveted to the hand frame member 14F. The pieces 46A and 46H are hingedly connected by hinge pin 48. The piece 46A includes a wide radial notch 50W and a narrow radial notch 50N as shown. The notches 50W and 50N are part of an adjustable stop arrangement further including holes 54A, 54B, 54C, and 54D spaced at 90° angles around the hinge pin 48. The holes 54A and 54B are disposed in piece 46H, whereas the holes 54C and 54D are shown for piece 46A. A hole is provided in piece 46H in registry with the position of hole 54C in FIG. 4. A screw 52, which functions as a stop pin, is shown disposed in the hole 54A.

With the stop pin or screw 52 disposed in hole 54A as shown in FIG. 4, the range of motion of hand member 14F relative to forearm member 12F is limited by the edges of the radial notch 50W. This radial notch 50W is preferably about 60°, thereby allowing a 30° range of motion in each direction from the position shown in FIG. 4. When the stop pin 52 is screwed into hole 54B, the narrow notch 50N determines the range of motion. The narrow notch 50N preferably has a total angle of about 30° (or 20°), thereby allowing a 15° (or 10°) movement of hand member 14F in each direction relative to the forearm member 12F. By placing the stop pin 52 in the hole 54C and the hole in piece 46A just underneath 54C in FIG. 4, hand member 14F will be locked approximately in line with forearm member 12F. By screwing the stop pin 52 into hole 54D and the hole in piece 46A underneath hole 54C in FIG. 4, hand member 14F and forearm member 12F may be locked at 90° to each other. The hole underneath hole 54C in FIG. 4 will, of course, be underneath and in registry with hole 54D after hand member 14F has been rotated 90° with respect to forearm member 12F.

An important feature of the hinge 16F and 16S is that they can be constructed of fiberglass resin or other material which is radiolucent. This allows an x-ray view in lateral direction without obstruction and without requiring removal of the brace. These materials also provide an inherent lubricity which facilitates smooth motion with the plastic heat fusable rivet hinge pin 48. The various frame members are preferably made of aluminum and would tend to block x-ray views, whereas the use of the fiberglass resin for the hinges 16F and 16H will avoid the need for brace removal prior to x-ray.

Obviously, the screw or stop pin 52 may be removed totally from any of the holes in the hinge 16F to allow a free range of motion between 14F and 12F. This range of motion is greater than 150° and may be considered as a first mode of operation, whereas the placement of stop pin 52 in either hole 54A or hole 54B can be considered as a second mode of operation with a narrow range of motion. The placement of pin 52 in either hole 54C or 54D can be considered a third mode of operation with the hand members 14F and 14S fixed to forearm members 12F and 12S.

As shown in FIGS. 1, 2 and 4, the present brace 10 is adapted to work with a standard forearm cast 60 including a notch 62 for accommodating the upper arm and allowing relative flexion-extension of the elbow. The configuration does not allow pronation-supination, i.e., rotation about the long axis of the forearm.

Operation

The present invention is useful for a distal radius fracture (especially in a patient below the age of 35 years) involving the articular surface of the radiocarpal joint and wherein the joint cannot be maintained in acceptable alignment by conventional methods.

Following closed reduction and sugar tong application to bring the bones into alignment from the above described fracture configuration, elective metacarpal pin placement is carried out. This is performed with the use of regional intravenous anesthesia. A long arm cast which terminates proximal to the radial and ulnar styloid with the forearm in supination is applied as soon as a satisfactory closed reduction has been achieved. The hinged frame and traction tubing or tensioners 26F and 26S attached to the metacarpal pin 20 are then incorporated into the long arm cast allowing for wrist motion, dorsiflexion, and palmarflexion. The slots 24F and 24S (not visible in the drawings) allow the traction tubing or tensioners 26F and 26S to distract the carpus and allow reduction of the fracture fragments. Post-cast brace radiographs are obtained to assess the alignment and indicate if any adjustments are necessary. A volar wrist splint comprising ORTHOPLAST or other moldable plastic splint material is fabricated and used between range of motion exercises. Appropriate tension on the pin 20 will be determined by the fracture configuration, soft tissue tolerance, and instability.

When a patient is wearing the brace 10 and the associated cast 60 the notch 62 will be disposed to allow flexion-extension of the elbow but blockage of pronation and supination. The hinge pin 48 in hinge 16F and the corresponding hinge pin in the hinge 16S will be placed in line with the patient's wrist joint. The transmetacarpal pin 20 will extend through the patient's hand and distract the patient's carpus by virtue of the adjustable tension placed on pin 20 by tensioners for traction tubing 26F and 26S.

As best shown in FIG. 3, the traction tubing or tensioner 26F (and 26S) may include a series of notches 58 which may be calibrated to allow for easy adjustment of the traction tension.

A more detailed outline or protocol of the operation steps may be presented as follows:

(1) Routine Bier Block (application of local anesthetic)
(2) Place Rolled Stockinette onto Proximal Forearm
(3) Place Fingers in Finger Traps with 10 Pounds Counter Traction Over the Arm
(4) Place Plastic Towel Drape Around Midforearm
(5) Prep Hand with Betadine (antiseptic)
(6) Pin Placement (The pin goes through second and third metacarpal bone)
  (a) 7/64 Threaded Pin
  (b) Abduct Thumb
  (c) Incise Skin at Junction Proximal/Middle ⅓ Second Metacarpal
  (d) Flex MP Joints Index-Ring Fingers
  (e) Insert Metacarpal Pin
(7) Reduce Fracture
(8) Locate Wrist Joint with Radiopaque Marker Taped on Radial Border (thumb side) of Wrist
(9) Check AP/Lateral x-rays
(10) Improve Reduction as Necessary
(11) Unroll Stockinette, Webril and Fiberglass Cast with Elbow in 90° Flexion and Forearm Supinated with Cast from Upper Arm to just Proximal to Styloid Processes
(12) Traction Maintained on Pin while Brace Applied with Center Axis of Hinge Corresponding to Axis of Wrist Joint, as Marked With Marker in #8 Above. Secure Hinges to Cast with Fiberglass Tape
(13) Adjust Tension Cords 26F and 26S to 2 Lbs. of Counter Traction (The actual tension can be varied depending on the physician's judgement with respect to fracture configuration, soft tissue tolerance and instability)
(14) Remove Countertraction and Recheck AP/Lateral x-ray
(15) If x-ray o.k., Release Tourniquet
(16) Trim and Cap Pins
(17) Followup
  (a) Fix hinge in Neutral (no motion allowed) for 3-5 days
  (b) Begin Active & Passive Finger Range of Motion Exercises as Soon as Possible
  (c) Begin 15° or 10° arc Wrist Motion at 3-5 Days (pin 52 in hole 54B)
  (d) Begin 30° arc Wrist Motion at 7-10 Days (pin 52 in hole 54A)
  (e) Begin Unlimited Wrist Motion at 14-18 Days
  (f) May Require Volar Wrist Splint when Restraints Removed for Night Use As noted in step 17 above the hinge of the present invention may be fixed for the first few days such that no wrist motion is allowed. The physician may increase the allowable range of motion by moving stop pin 52 as the healing process gets underway.

Although the present description has included specific construction details and materials, it will be readily understood that these are for illustrative purposes only. Various modifications and adaptations will be readily apparent to those of ordinary skill in the art. Accordingly, the scope of the present invention should be determined by reference to the claims appended hereto.

What is claimed is:

1. A dynamic traction wrist cast brace comprising:
  (a) first and second forearm frame members disposed on opposite sides of a forearm cast;
  (b) first and second hand frame members;
  (c) first and second hinges respectively pivotably connecting said first and second forearm frame members to said first and second hand frame members, said first and second hinges operable to allow patient wrist motion;
  (d) a transmetacarpal pin mounted to said first and second hand frame members and having first and second sides respectively slidably mounted to said first and second hand frame members, said transmetacarpal pin operable to cause said first and second hand frame members to track movement of a patient's hand; and
  (e) first and second tensioners respectively attached to first and second sides of said transmetacarpal pin.

2. The dynamic traction wrist cast brace of claim 1 further comprising first and second end frame members adjustably attached together and adjustably mounted to said respective first and second hand frame members such that the width and length of said brace can be adjusted to fit a particular patient.

3. The dynamic traction wrist case brace of claim 2 wherein said first and second end frame members are each adjustably mounted to said respective first and second hand frame members by a series of sequential holes.

4. The dynamic traction wrist cast brace of claim 1 wherein said transmetacarpal pin is mounted in first and second slots respectively disposed in said first and second hand frame members.

5. The dynamic traction wrist cast brace of claim 1 wherein said first and second hinges include respective first and second adjustable stop arrangements.

6. The dynamic traction wrist cast brace of claim 5 wherein said first and second adjustable stop arrangements are each disposable in at least:
  (i) a first mode allowing said first and second hand frame members to move at least over a 150° range of motion relative to said first and second forearm frame members;
  (ii) a second mode with a range of motion less than in said first mode; and
  (iii) a third mode wherein said first and second hand frame members are fixed relative to said first and second forearm frame members.

7. The dynamic traction wrist cast brace of claim 5 wherein said first and second adjustable stop arrangements each includes a wide radial notch and a narrow radial notch and at least two stop pin receiving holes, and wherein the range of motion of said brace is limited by said wide radial notch when a stop pin is in one of said stop pin receiving holes and the range of motion of said brace is limited by said narrow radial notch when a stop pin is in the other of said stop pin receiving holes.

8. The dynamic traction wrist case brace of claim 1 wherein said first and second hinges extend respectively between said first and second forearm frame members and said first and second hand frame members, and said first and second hinges are made of radiolucent material such that an x-ray may be made of a patient's wrist without removal of said brace.

9. The dynamic traction wrist cast brace of claim 1 wherein each of said first and second tensioners is an elastic band adjustably mounted to an end portion extending between said first and second hand frame members.

10. A dynamic traction wrist brace comprising:

(a) first and second forearm frame members for disposal on opposite sides of a forearm cast;
(b) first and second hand frame members;
(c) first and second hinges respectively pivotably connecting said first and second forearm frame members to said first and second hand frame members, said first and second hinges operable to allow patient wrist motion;
(d) an end portion extending between said first and second hand frame members; and
(e) a transmetacarpal pin mounted to said first and second hand frame members and slidable in slots in said first and second hand frame members, said transmetacarpal pin operable to cause said first and second hand frame members to track movement of a patient's hand.

11. The dynamic traction wrist brace of claim 10 further comprising first and second tensioners respectively attached to first and second sides of said transmetacarpal pin and adjustably mounted to said end portion.

12. The dynamic traction wrist brace of claim 11 wherein said end portion comprises first and second end frame members adjustably attached together and adjustably mounted to said respective first and second hand frame members such that the width and length of said brace can be adjusted to fit a particular patient.

13. The dynamic traction wrist brace of claim 12 wherein said first and second end frame members are each adjustably mounted to said respective first and second hand frame members by a series of sequential holes.

14. The dynamic traction wrist brace of claim 11 wherein said first and second hinges include respective first and second adjustable stop arrangements.

15. The dynamic traction wrist brace of claim 14 wherein said first and second adjustable stop arrangements each includes a wide radial notch and a narrow radial notch and at least two stop pin receiving holes, and wherein the range of motion of said brace is limited by said wide radial notch when a stop pin is in one of said stop pin receiving holes and the range of motion of said brace is limited by said narrow radial notch when a stop pin is in the other of said stop pin receiving holes.

16. A dynamic traction wrist brace comprising:
(a) first and second forearm frame members for disposal on opposite sides of a forearm cast;
(b) first and second hand frame members, said first and second hand frame members respectively attached to said first and second forearm frame members and allowing patient wrist motion;
(c) an end portion extending between said first and second hand frame members;
(d) a transmetacarpal pin mounted to said first and second hand frame members and slidable in slots in said first and second hand frame members, said transmetacarpal pin operable to cause said first and second hand frame members to track movement of a patient's hand;
(e) first and second tensioners respectively attached to first and second sides of said transmetacarpal pin; and
(f) first and second end frame members adjustably attached together and adjustably mounted to said respective first and second hand frame members such that the width and length of said brace can be adjusted to fit a particular patient.

17. The dynamic traction wrist brace of claim 16 wherein said first and second end frame members are each adjustable mounted to said respective first and second hand frame members by a series of sequential holes.

18. The dynamic traction wrist brace of claim 16 wherein each of said first and second tensioners is an elastic band adjustably mounted to one of said first and second end frame members.

19. The dynamic traction wrist brace of claim 18 further comprising first and second hinges respectively pivotably connecting said first and second forearm frame members to said first and second hand frame members, said first and second hinges operable to allow wrist motion, and wherein said first and second hinges extend respectively between said first and second forearm frame members and said first and second hand frame members, and said first and second hinges are made of radiolucent material such that an x-ray may be made of a patient's wrist without removal of said brace.

20. The dynamic traction wrist brace of claim 18 further comprising first and second hinges respectively pivotably connecting said first and second forearm frame members to said first and second hand frame members, said first and second hinges operable to allow wrist motion, and wherein said first and second hinges are each disposable in at least:
(i) a first mode allowing said first and second hand frame members to move at least over a 150° range of motion relative to said first and second forearm frame members; and
(ii) a second mode with a range of motion less than in said first mode.

21. In a method for the treatment of a fractured bone requiring providing distal traction on the hand and wrist of a human, the improvement comprising placing the hand and wrist of said human in the dynamic traction wrist cast brace of claim 1 or in the dynamic traction wrist brace of claim 10 or claim 16.

* * * * *